(12) United States Patent
Son et al.

(10) Patent No.: US 11,848,420 B2
(45) Date of Patent: Dec. 19, 2023

(54) COMPOUND, ELECTROLYTE SOLUTION FOR SECONDARY BATTERY COMPRISING SAME, AND SECONDARY BATTERY COMPRISING SAME

(71) Applicant: DONGWHA ELECTROLYTE CO., LTD., Chungcheongnam-do (KR)

(72) Inventors: Bum Suk Son, Daejeon (KR); Jae Wook Shin, Daejeon (KR); Hyun Seok Ahn, Incheon (KR); Yu Rim Been, Daejeon (KR)

(73) Assignee: DONGWHA ELECTROLYTE CO., LTD., Chungcheongnam-do (KR)

( * ) Notice: Subject to any disclaimer, the term of this patent is extended or adjusted under 35 U.S.C. 154(b) by 0 days.

(21) Appl. No.: 18/027,450

(22) PCT Filed: Nov. 30, 2021

(86) PCT No.: PCT/KR2021/017825
§ 371 (c)(1),
(2) Date: Mar. 21, 2023

(87) PCT Pub. No.: WO2023/286940
PCT Pub. Date: Jan. 19, 2023

(65) Prior Publication Data
US 2023/0335796 A1    Oct. 19, 2023

(30) Foreign Application Priority Data

Jul. 14, 2021  (KR) .................. 10-2021-0092197
Nov. 29, 2021  (KR) .................. 10-2021-0166583

(51) Int. Cl.
*H01M 10/0567*  (2010.01)
*C07F 9/6596*  (2006.01)
(Continued)

(52) U.S. Cl.
CPC ....... *H01M 10/0567* (2013.01); *C07F 9/6596* (2013.01); *H01M 10/052* (2013.01);
(Continued)

(58) Field of Classification Search
None
See application file for complete search history.

(56) References Cited

U.S. PATENT DOCUMENTS

2005/0283027 A1* 12/2005 Grutzmacher ........ C07F 9/6568
568/9
2020/0136185 A1*  4/2020 Ji ...................... H01M 10/0525

FOREIGN PATENT DOCUMENTS

CN          116143666 A  *  5/2023
KR    10-2015-0069836 A       6/2015
(Continued)

OTHER PUBLICATIONS

International Search Report for PCT/KR2021/017825 dated Apr. 12, 2022.
(Continued)

*Primary Examiner* — Jeremiah R Smith
(74) *Attorney, Agent, or Firm* — The PL Law Group, PLLC

(57) ABSTRACT

A compound according to an embodiment is represented by Formula 1. An electrolyte includes a lithium salt, an organic solvent, and the compound. A lithium secondary battery includes a cathode, an anode disposed to face the cathode, a separation membrane interposed between the cathode and the anode, and the electrolyte. In a method for preparing the compound, a compound represented by Formula 2 and a compound represented by Formula 3 are reacted.

13 Claims, 3 Drawing Sheets

(51) Int. Cl.
*H01M 10/052* (2010.01)
*C07F 9/6564* (2006.01)
*C07C 211/05* (2006.01)
*C07F 9/547* (2006.01)
*H01M 10/0525* (2010.01)

(52) U.S. Cl.
CPC ............ *C07C 211/05* (2013.01); *C07F 9/547* (2013.01); *C07F 9/6564* (2013.01); *H01M 10/0525* (2013.01)

(56) References Cited

FOREIGN PATENT DOCUMENTS

| KR | 10-1999615 B1 | 7/2019 |
| KR | 10-2021-0064175 A | 6/2021 |

OTHER PUBLICATIONS

Testa, M. L. et al., "Use of zirconium phosphate-sulphate as acid catalyst for synthesis of glycerol-based fuel additives", Catalysts, 2019, vol. 9, No. 148 (inner pp. 1-12).

Blasse, G. et al., "The luminescence of f:I—Zr2(PO4)2SO4 in comparison to that of isomorphous SC2(WO4)3", Chemical Physics Letters, Jun. 17, 1988, vol. 147, No. 5, pp. 514-516.

Alamo, J. et al., "Zirconium phospho-sulfates with NaZr2(PO4)3-type stmcture", Journal of Solid State Chemistry, 1984, vol. 51, pp. 270-273.

\* cited by examiner

COMPOUND, ELECTROLYTE SOLUTION FOR SECONDARY BATTERY COMPRISING SAME, AND SECONDARY BATTERY COMPRISING SAME

CROSS REFERENCE TO RELATED APPLICATIONS AND CLAIM OF PRIORITY

This application claims benefit under 35 U.S.C. 119, 120, 121, or 365(c), and is a National Stage entry from International Application No. PCT/KR2021/017825 filed on Nov. 30, 2021, which claims priority to the benefit of Korean Patent Application Nos. 10-2021-0092197 filed in the Korean Intellectual Property Office on Jul. 14, 2021 and 10-2021-0166583 filed in the Korean Intellectual Property Office on Nov. 29, 2021, the entire contents of which are incorporated herein by reference.

BACKGROUND

1. Technical Field

The present invention relates to a novel compound, an electrolyte for a secondary battery including the compound, and a secondary battery including the electrolyte.

2. Background Art

A secondary battery is a battery which can be repeatedly charged and discharged, and has been applied to small electronic devices such as a mobile phone, a laptop computer, etc., as a power source thereof.

In particular, a lithium secondary battery has a high operating voltage and a high energy density, and is advantageous in terms of a rapid charging speed and light weight. Thereby, the lithium secondary battery is applied to electric vehicles as well as small electronic devices as a power source thereof.

For example, in order for the lithium secondary battery to be used as a power source for an electric vehicle, it should have better output characteristics and life-span characteristics.

Meanwhile, the lithium secondary battery may include an anode including an anode active material (e.g., graphite); a cathode including a cathode active material (e.g., lithium metal oxide particles); and a non-aqueous electrolyte including a lithium salt and an organic solvent.

For example, in the lithium secondary battery, a process of intercalating and deintercalating lithium ions from lithium metal oxide particles and graphite is repeated, such that charging and discharging may be performed.

For example, the output characteristics and life-span characteristics of the lithium secondary battery may be improved by varying the composition of the electrolyte. For example, the output characteristics of the lithium secondary battery may be improved by enhancing the conductivity of lithium ions. In addition, the life-span characteristics of the lithium secondary battery may be improved by firmly forming a solid electrolyte interface (SEI) film on the anode.

Korean Patent Registration Publication No. 10-1999615 discloses an electrolyte for a lithium secondary battery, which can improve the life-span characteristics of the lithium secondary battery.

SUMMARY

An object of the present invention is to provide a novel compound.

In addition, another object of the present invention is to provide an electrolyte including the compound for a lithium secondary battery, which may improve life-span characteristics (e.g., capacity retention rate during repeated charging and discharging), output characteristics, and the like of the lithium secondary battery.

Further, another object of the present invention is to provide a lithium secondary battery including the electrolyte, which has improved life-span characteristics, output characteristics and the like.

To achieve the above objects, according to an aspect of the present invention, there is provided a compound represented by formula 1 below:

[Formula 1]

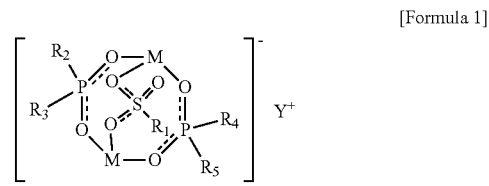

wherein, in Formula 1, $R_1$ is a substituted or unsubstituted C1-C6 alkyl group; a substituted or unsubstituted C2-C6 alkenyl group; a substituted or unsubstituted C2-C6 alkynyl group; a substituted or unsubstituted C3-C7 cycloalkyl group; a substituted or unsubstituted C3-C7 cycloalkenyl group; or $-OR_1$; $R_2$ to $R_5$ are each independently halogen; or a substituted or unsubstituted C1-C6 alkyl group, M is alkali metal, and $Y^+$ is a cationic material.

In one embodiment, $R_1$ may be a substituted or unsubstituted C1-C6 alkyl group; or a substituted or unsubstituted C2-C6 alkenyl group, at least one of $R_2$ to $R_5$ may be halogen, M may be Li, Na or K; and $Y^+$ may be $N^+R_aR_bR_cR_d$, and at least one of Ra to Rd may be hydrogen.

In one embodiment, $R_1$ may be a substituted or unsubstituted C2-C6 alkenyl group, all of $R_2$ to $R_5$ may be halogen, M may be Li, $Y^+$ may be $N^+R_aR_bR_cR_d$, Ra may be hydrogen, and Rb to Rd may be each independently a C1-C3 alkyl group.

In addition, according to another aspect of the present invention, there is provided a method for preparing the compound mentioned above, including reacting a compound represented by Formula 2 below with a compound represented by Formula 3 below:

[Formula 2]

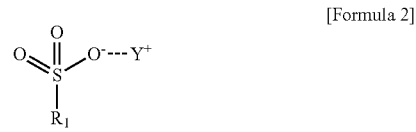

wherein, in Formula 2, $R_1$ is a substituted or unsubstituted C1-C6 alkyl group; a substituted or unsubstituted C2-C6 alkenyl group; a substituted or unsubstituted C2-C6 alkynyl group; a substituted or unsubstituted C3-C7 cycloalkyl group; a substituted or unsubstituted C3-C7 cycloalkenyl group; or $-OR_1$, and $Y^+$ is a cationic material.

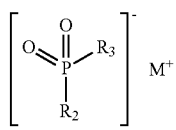

[Formula 3]

wherein, in Formula 3, $R_2$ and $R_3$ are each independently halogen; or a substituted or unsubstituted C1-C6 alkyl group, and $M^+$ is an alkali metal ion.

Further, according to another aspect of the present invention, there is provided an electrolyte for a lithium secondary battery including: a lithium salt; an organic solvent; and a compound represented by Formula 1 above.

In one embodiment, a content of the compound represented by Formula 1 may be 0.01 to 10% by weight based on a total weight of the electrolyte.

In one embodiment, the organic solvent includes at least one of a linear carbonate-based solvent, a cyclic carbonate-based solvent, a linear ester-based solvent, a cyclic ester-based solvent, an ether-based solvent, a ketone-based solvent, an alcohol-based solvent, and an aprotic solvent.

In one embodiment, the electrolyte may further include an auxiliary additive including at least one of a fluorine-containing cyclic carbonate-based compound, a vinyl group-containing cyclic carbonate-based compound, a vinylene carbonate-based compound, a cyclic sulfate-based compound, a sultone-based compound, a fluorine-containing lithium phosphate-based compound, a lithium borate-based compound, a lactone-based compound and a sulfonyl imide-based compound.

In one embodiment, a content of the auxiliary additive may be 0.01 to 10% by weight based on the total weight of the electrolyte.

In one embodiment, a ratio of the content of the auxiliary additive to the content of the compound represented by Formula 1 in the electrolyte may be 0.1 to 10.

Furthermore, according to another aspect of the present invention, there is provided a lithium secondary battery including: a cathode; an anode disposed to face the cathode; a separation membrane interposed between the cathode and the anode; and the electrolyte for a lithium secondary battery according to exemplary embodiments.

According to exemplary embodiments, the compound represented by Formula 1 may be included in the electrolyte for a lithium secondary battery.

The electrolyte for a lithium secondary battery according to exemplary embodiments may include the compound represented by Formula 1, such that life-span characteristics (e.g., capacity retention rate during repeated charging and discharging) and output characteristics of the lithium secondary battery may be improved.

DETAILED DESCRIPTION

Figure 1:
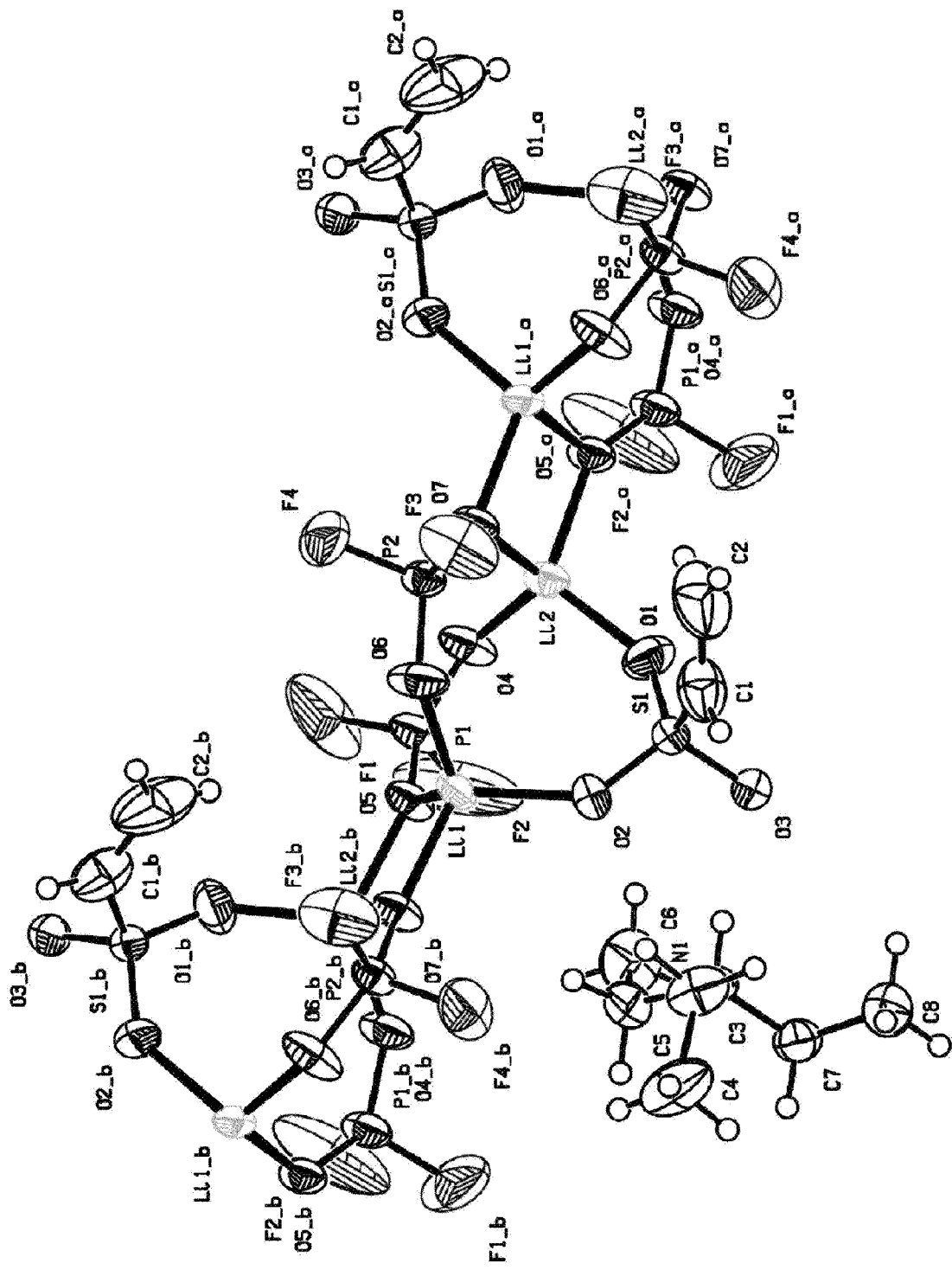
FIG. 1 is a diagram illustrating a three-dimensional structure of a compound of Preparative Example 1 analyzed by single crystal X-ray diffraction (SC-XRD).

According to the present invention, there are provided a novel compound represented by Formula 1, an electrolyte for a lithium secondary battery including the compound, and a lithium secondary battery including the electrolyte.

As used herein, the "X-based compound" may refer to a compound including an X unit in a matrix, a pendant group or a substituent.

As used herein, the "Ca-Cb" may refer to "the number of carbon atoms of a to b." In addition, the "5- to 7-membered rings" may refer to the case where "the number of atoms in the ring is 5 to 7."

<Novel Compound>

The novel compound according to the present invention may be represented by Formula 1 below.

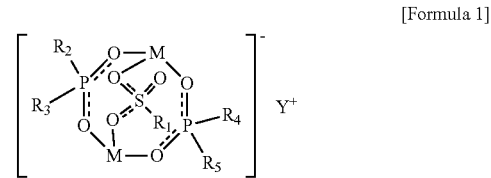

[Formula 1]

In Formula 1, $R_1$ may be a substituted or unsubstituted C1-C6 alkyl group; a substituted or unsubstituted C2-C6 alkenyl group; a substituted or unsubstituted C2-C6 alkynyl group; a substituted or unsubstituted C3-C7 cycloalkyl group; a substituted or unsubstituted C3-C7 cycloalkenyl group; or —$OR_1$.

$R_2$ to $R_5$ may be each independently halogen; or a substituted or unsubstituted C1-C6 alkyl group.

M may be alkali metal, and $Y^+$ may be a cationic material.

For example, bonds "⋯" between phosphorus (P) and oxygen (O); and between sulfur (S) and oxygen (O) may represent that some electrons are delocalized.

For example, the meaning of "substituted" may mean that a hydrogen atom is substituted with an optional substituent, such that the optional substituent is further bonded to the corresponding substituent.

For example, the optional substituent may be a halogen, a C1-C6 alkyl group, a C2-C6 alkenyl group, a C2-C6 alkynyl group, a C1-C6 alkoxy group, a nitro group, a cyano group and the like. In some embodiments, the optional substituent may be a halogen or a C1-C6 alkyl group.

In one embodiment, $R_1$ may be a substituted or unsubstituted C1-C6 alkyl group; or a substituted or unsubstituted C2-C6 alkenyl group.

In some embodiments, $R_1$ may be a substituted or unsubstituted C2-C6 alkenyl group. In some embodiments, $R_1$ may be an unsubstituted C2-C6 alkenyl group.

In one embodiment, at least one of $R_2$ to $R_5$ may be halogen (e.g., F, Cl, Br or I). In some embodiments, at least one of $R_2$ to $R_5$ may be F.

In one embodiment, all of $R_2$ to $R_5$ may be halogen. In some embodiments, all of $R_2$ to $R_5$ may be F.

In one embodiment, M may be Li, Na or K.

In one embodiment, $Y^+$ may be an alkali metal ion; an ammonium ion; or primary to quaternary ammonium ions.

In some embodiments, $Y^+$ may be $N^+R_aR_bR_cR_d$ or $R_eR_fN^+=R_gR_h$.

$R_a$ to $R_d$ may be each independently hydrogen; a substituted or unsubstituted C1-C6 alkyl group; or a substituted or unsubstituted C2-C6 alkenyl group. In addition, at least two of $R_a$ to $R_d$ may be bonded to each other to form 5- to 7-membered hetero rings.

$R_e$ to $R_h$ may be each independently hydrogen; a substituted or unsubstituted C1-C6 alkyl group; or a substituted or unsubstituted C2-C6 alkenyl group. In addition, at least two of $R_e$ to $R_h$ may be bonded to each other to form 5- to 7-membered hetero rings.

In some embodiments, $Y^+$ may be $N^+R_aR_bR_cR_d$, and at least one of $R_a$ to $R_d$ may be hydrogen. In some embodiments, $Y^+$ may be $N^+R_aR_bR_cR_d$, $R_a$ may be hydrogen, and $R_b$ to $R_d$ may be each independently a C1-C3 alkyl group.

<Method for Preparing a Novel Compound>

According to exemplary embodiments, the compound of Formula 1 may be prepared by reacting a sulfonate-based salt or a sulfate-based salt with an alkali metal phosphate-based salt.

In one embodiment, the sulfonate-based salt or sulfate-based salt may be represented by Formula 2 below.

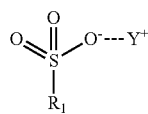

[Formula 2]

In Formula 2, $R_1$ may be a substituted or unsubstituted C1-C6 alkyl group; a substituted or unsubstituted C2-C6 alkenyl group; a substituted or unsubstituted C2-C6 alkynyl group; a substituted or unsubstituted C3-C7 cycloalkyl group; a substituted or unsubstituted C3-C7 cycloalkenyl group; or $-OR_1$. $Y^+$ may be a cationic material.

In one embodiment, $R_1$ may be a substituted or unsubstituted C1-C6 alkyl group; or a substituted or unsubstituted C2-C6 alkenyl group.

In some embodiments, $R_1$ may be a substituted or unsubstituted C2-C6 alkenyl group. In some embodiments, $R_1$ may be an unsubstituted C2-C6 alkenyl group.

In one embodiment, $Y^+$ may be an alkali metal ion; an ammonium ion; or primary to quaternary ammonium ions.

In some embodiments, $Y^+$ may be $N^+R_aR_bR_cR_d$ or $R_eR_fN^+=R_gR_h$.

$R_a$ to $R_d$ may be each independently hydrogen; a substituted or unsubstituted C1-C6 alkyl group; or a substituted or unsubstituted C2-C6 alkenyl group. In addition, at least two of $R_a$ to $R_d$ may be bonded to each other to form 5- to 7-membered hetero rings.

$R_e$ to $R_h$ may be each independently hydrogen; a substituted or unsubstituted C1-C6 alkyl group; or a substituted or unsubstituted C2-C6 alkenyl group. In addition, at least two of $R_e$ to $R_h$ may be bonded to each other to form 5- to 7-membered hetero rings.

In some embodiments, $Y^+$ may be $N^+R_aR_bR_cR_d$, and at least one of $R_a$ to $R_d$ may be hydrogen. In some embodiments, $Y^+$ may be $N^+R_aR_bR_cR_d$, $R_a$ may be hydrogen, and $R_b$ to $R_d$ may be each independently a C1-C3 alkyl group.

In one embodiment, $R_a$ may be a substituted or unsubstituted C1-C6 alkyl group; or a substituted or unsubstituted C2-C6 alkenyl group.

In some embodiments, $R_a$ may be a substituted or unsubstituted C2-C6 alkenyl group. In some embodiments, $R_a$ may be an unsubstituted C2-C6 alkenyl group.

In one embodiment, the alkali metal phosphate-based salt may be represented by Formula 3 below.

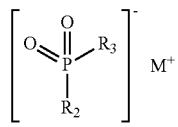

[Formula 3]

In Formula 3, $R_2$ and $R_3$ may be each independently halogen (e.g., F, Cl, Br or I); or a substituted or unsubstituted C1-C6 alkyl group.

In one embodiment, at least one of $R_2$ and $R_3$ may be halogen. In some embodiments, at least one of $R_2$ and $R_3$ may be F.

In one embodiment, both of $R_2$ and $R_3$ may be halogen. In some embodiments, both of $R_2$ and $R_3$ may be F.

In one embodiment, crystals generated by reacting the sulfonate-based salt or sulfate-based salt with the alkali metal phosphate-based salt may be filtered and dried to obtain the compound represented by Formula 1.

In one embodiment, the reaction temperature may be 10 to 50° C.

In one embodiment, a mixing molar ratio of the sulfonate-based salt or sulfate-based salt with the alkali metal phosphate-based salt may be 1:0.9 to 1:1.1.

<Electrolyte for a Lithium Secondary Battery>

According to exemplary embodiments of the present invention, there is provided an electrolyte for a lithium secondary battery including the compound represented by Formula 1 above.

In one embodiment, the compound represented by Formula 1 may be provided as an additive of the electrolyte for a lithium secondary battery.

The lithium secondary battery according to the exemplary embodiments may include the electrolyte for a lithium secondary battery, such that life-span characteristics (e.g., capacity retention rate during repeated charging and discharging), output characteristics, and the like may be improved.

For example, the compound represented by Formula 1 may be reduced and decomposed at a voltage of about 2.1 V to form a solid electrolyte interface (SEI) film on the surface of an anode. The SEI film may suppress decomposition of an organic solvent (e.g., ethylene carbonate, etc.) generated at a voltage of 2.9 V. Accordingly, the life-span characteristics of the lithium secondary battery may be improved.

For example, the compound represented by Formula 1 may reduce a cathode interface resistance. Accordingly, the output characteristics of the lithium secondary battery may be improved.

The electrolyte for a lithium secondary battery according to exemplary embodiments may include a lithium salt (however, the lithium salt form of the compound represented by Formula 1 is excluded); an organic solvent; and the compound represented by Formula 1.

In one embodiment, a content of the compound represented by Formula 1 may be 0.01 to 10% by weight ("wt. %"), preferably 0.1 to 7.5 wt. %, and more preferably 0.3 to 5 wt. % based on a total weight of the electrolyte. Within the above range, the life-span characteristics and output characteristics of the lithium secondary battery may be further improved.

For example, the compound represented by Formula 1 may exist as a monomer in the electrolyte, and may exist in the form of a dimer (e.g., see Formula 4 below, substituents will not be described), a trimer, or a multimer such as a tetramer or more.

[Formula 4]

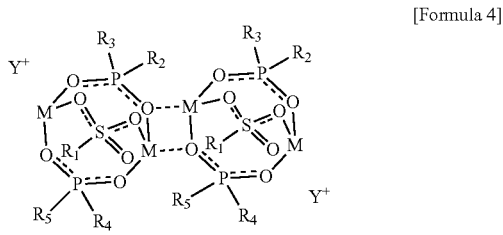

In one embodiment, the electrolyte for a lithium secondary battery may further include an auxiliary additive to further improve the life-span characteristics and output characteristics of the lithium secondary battery, or to improve high temperature storage characteristics and the like.

For example, the auxiliary additive may include a fluorine-containing cyclic carbonate-based compound, a vinyl group-containing cyclic carbonate-based compound, a vinylene carbonate-based compound, a cyclic sulfate-based compound, a sultone-based compound, a fluorine-containing lithium phosphate-based compound, a lithium borate-based compound, a lactone-based compound, a sulfonyl imide-based compound and the like.

In some embodiments, a content of the auxiliary additive may be 0.01 to 10 wt. %, 0.1 to 7.5 wt. %, or 0.3 to 5 wt. % based on the total weight of the electrolyte. Within the above range, the life-span characteristics, the output characteristics, the high temperature storage characteristics, and the like of the lithium secondary battery may be further improved.

In some embodiments, a ratio of the content of the auxiliary additive to the content of the compound represented by Formula 1 in the total weight of the electrolyte may be 0.1 to 10, preferably 0.1 to 7, and more preferably 0.5 to 5.

For example, the fluorine-containing cyclic carbonate-based compound may have a 5- to 7-membered cyclic structure. For example, in the fluorine-containing cyclic carbonate-based compound, a fluorine atom may be directly bonded to a carbon atom, or a fluorine-substituted alkyl group (e.g., —CF$_3$, etc.) may be bonded thereto.

In some embodiments, the fluorine-containing cyclic carbonate-based compound may include fluoroethylene carbonate (FEC) and the like.

In some embodiments, a content of the fluorine-containing cyclic carbonate-based compound may be 0.01 to 2 wt. %, or 0.1 to 1 wt. % based on the total weight of the electrolyte.

In some embodiments, the vinyl group-containing cyclic carbonate-based compound may include vinyl ethylene carbonate (VEC) and the like. In addition, the vinylene carbonate-based compound may include vinylene carbonate (VC) and the like.

In some embodiments, a content of the vinyl group-containing cyclic carbonate-based compound may be 0.01 to 2 wt. %, or 0.1 to 1 wt. % based on the total weight of the electrolyte. In addition, a content of the vinylene carbonate-based compound may be 0.01 to 2 wt. %, or 0.1 to 1 wt. % based on the total weight of the electrolyte.

For example, the cyclic sulfate-based compound may have a 5- to 7-membered cyclic structure. In some embodiments, the cyclic sulfate-based compound may include ethylene sulfate (ESA), trimethylene sulfate (TMS), methyltrimethylene sulfate (MTMS), 1,3-propanediol cyclic sulfate and the like.

In some embodiments, the cyclic sulfate-based compound may include a bicyclic sulfate-bated compound. In some embodiments, the bicyclic sulfate-based compound may include 2,4,8,10-Tetraoxa-3,9-dithiaspiro[5.5]undecane 3,3,9,9-tetraoxide, 4,4'-bi(1,3,2-dioxathiolane)]2,2,2',2'-tetraoxide and the like.

In some embodiments, a content of the cyclic sulfate-based compound may be 0.01 to 2 wt. %, or 0.1 to 1 wt. % based on the total weight of the electrolyte.

For example, the sultone-based compound may have a 5- to 7-membered cyclic structure. In some embodiments, the sultone-based compound may include at least one of an alkyl sultone-based compound and an alkenyl sultone-based compound. For example, the alkyl sultone-based compound may have only a saturated bond in a ring, and the alkenyl sultone-based compound may include a double bond in the ring.

In some embodiments, the alkyl sultone-based compound may include 1,3-propane sultone (PS), 1,4-butane sultone and the like. In addition, the alkenyl sultone-based compound may include ethene sultone, 1,3-propene sultone (PRS), 1,4-butene sultone, 1-methyl-1,3-propene sultone and the like.

In some embodiments, a content of the sultone-based compound may be 0.01 to 2 wt. %, or 0.1 to 1 wt. % based on the total weight of the electrolyte.

For example, in the fluorine-containing lithium phosphate-based compound, a fluorine atom may be directly bonded to a phosphorus atom, or a fluorine-substituted alkyl group (e.g., —CF$_3$) may be bonded thereto.

In some embodiments, the fluorine-containing lithium phosphate-based compound may include lithium difluorophosphate, lithium tetrafluoro oxalate phosphate, lithium difluorobis(oxalato)phosphate and the like.

In some embodiments, a content of the fluorine-containing lithium phosphate-based compound may be 0.01 to 2 wt. %, or 0.1 to 1 wt. % based on the total weight of the electrolyte.

In some embodiments, the lithium borate-based compound may include lithium tetraphenylborate, lithium bis(oxalato)borate (LiBOB), lithium difluoro(oxalato)borate (LiFOB) and the like.

In some embodiments, a content of the lithium borate-based compound may be 0.01 to 2 wt. %, or 0.1 to 1 wt. % based on the total weight of the electrolyte.

In some embodiments, the lactone-based compound may include at least one of a bicyclo lactone-based compound and a lactone-based compound including a double bond in a ring. In some embodiments, the lactone-based compound may include muconic lactone and the like.

In some embodiments, a content of the lactone-based compound may be 0.01 to 2 wt. %, or 0.1 to 1 wt. % based on the total weight of the electrolyte.

In some embodiments, the sulfonyl imide-based compound may include lithium bis(fluorosulfonyl)imide and the like.

In some embodiments, a content of the sulfonyl imide-based compound may be 0.01 to 2 wt. %, or 0.1 to 1 wt. % based on the total weight of the electrolyte.

For example, the organic solvent may have sufficient solubility to the lithium salt, the compound represented by Formula 1, and the auxiliary additive. In one embodiment, the organic solvent may be a non-aqueous organic solvent.

In one embodiment, the organic solvent may include a carbonate-based solvent, an ester-based (carboxylate-based) solvent, an ether-based solvent, a ketone-based solvent, an alcohol-based solvent, an aprotic solvent and the like.

In some embodiments, the carbonate-based solvent may include a linear carbonate-based solvent and a cyclic carbonate-based solvent.

For example, the linear carbonate-based solvent may include dimethyl carbonate (DMC), ethyl methyl carbonate (EMC), diethyl carbonate (DEC), methyl propyl carbonate, ethyl propyl carbonate, dipropyl carbonate and the like.

For example, the cyclic carbonate-based solvent may include ethylene carbonate (EC), propylene carbonate (PC), butylene carbonate and the like.

In some embodiments, the organic solvent may include the linear carbonate-based solvent more than the cyclic carbonate-based solvent based on a volume.

For example, in the organic solvent, a volume ratio of the cyclic carbonate-based solvent to the linear carbonate-based solvent may be 1:1 to 9:1, and preferably 1.5:1 to 4:1.

In some embodiments, the ester-based solvent may include a linear ester-based solvent and a cyclic ester-based solvent.

For example, the linear ester-based solvent may include methyl propionate, ethyl propionate, propyl acetate, butyl acetate, ethyl acetate and the like.

For example, the cyclic ester-based solvent may include butyrolactone, caprolactone, valerolactone and the like.

For example, the ether-based solvent may include at least one of dibutyl ether, tetraethylene glycol dimethyl ether (TEGDME), diethylene glycol dimethyl ether (DEGDME), dimethoxyethane, tetrahydrofuran (THF), and 2-methyltetrahydrofuran.

For example, the ketone-based solvent may include cyclohexanone and the like.

For example, the alcohol-based solvent may include at least one of ethyl alcohol and isopropyl alcohol.

For example, the aprotic solvent may include at least one of a nitrile-based solvent, an amide-based solvent (e.g., dimethylformamide), a dioxolane-based solvent (e.g., 1,3-dioxolane), and a sulfolane-based solvent.

In some embodiments, the organic solvent may include the carbonate-based solvent, and the carbonate-based solvent may include at least one of ethylene carbonate (EC), ethylmethyl carbonate (EMC), dimethyl carbonate (DMC), and diethyl carbonate (DEC).

For example, the lithium salt may be represented by $Li^+X^-$.

In one embodiment, the anion ($X^-$) of the lithium salt may include $F^-$, $Cl^-$, $Br^-$, $I^-$, $NO_3^-$, $N(CN)_2^-$, $BF_4^-$, $ClO_4^-$, $PF_6^-$, $(CF_3)_2PF_4^-$, $(CF_3)_3PF_3^-$, $(CF_3)_4PF_2^-$, $(CF_3)_5PF^-$, $(CF_3)_6P^-$, $CF_3SO_3^-$, $CF_3CF_2SO_3^-$, $(CF_3SO_2)_2N^-$, $(FSO_2)_2N^-$, $CF_3CF_2(CF_3)_2CO^-$, $(CF_3SO_2)_2CH^-$, $(SF_5)_3C^-$, $(CF_3SO_2)_3C^-$, $CF_3(CF_2)_7SO_3^-$, $CF_3CO_2^-$, $CH_3CO_2^-$, $SCN^-$, $(CF_3CF_2SO_2)_2N^-$ and the like.

In some embodiments, the lithium salt may include $LiPF_6$, $LiBF_4$, $LiSbF_6$, $LiAsF_6$, $LiClO_4$, $LiN(C_2F_5SO_2)_2$, $LiN(CF_3SO_2)_2$, $CF_3SO_3Li$, $LiC(CF_3SO_2)_3$ and the like.

In one embodiment, the lithium salt may be included in a concentration of 0.01 to 5 M, and preferably 0.01 to 2 M based on the organic solvent. Within the above concentration range, lithium ions and/or electrons may smoothly move during charging and discharging of the battery.

<Lithium Secondary Battery>

According to exemplary embodiments of the present invention, there is provided a lithium secondary battery including the electrolyte for a lithium secondary battery.

Figure 2:
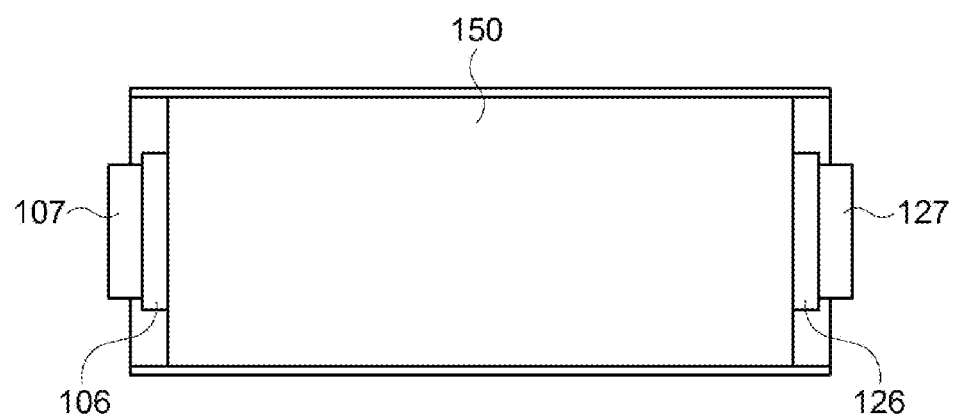
FIGS. 2 and 3 are a plan perspective view and a cross-sectional view schematically illustrating a lithium secondary battery according to exemplary embodiments, respectively.
Figure 3:
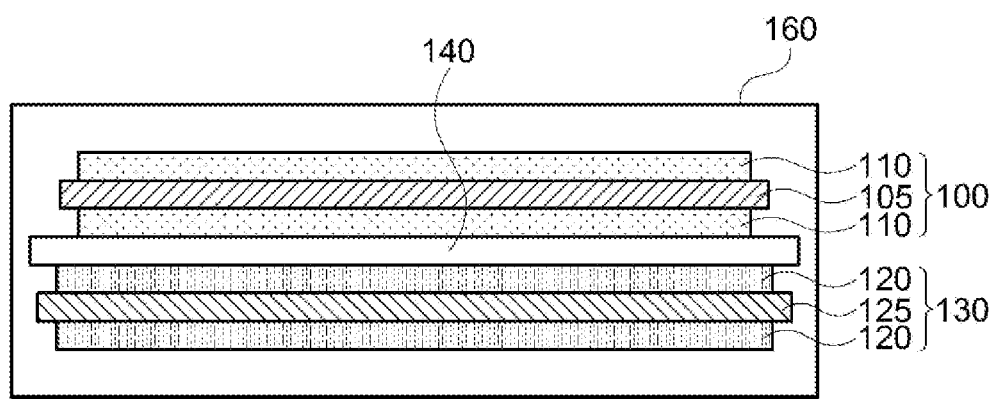

Hereinafter, a lithium secondary battery according to exemplary embodiments will be described in more detail with reference to the drawings. FIGS. 2 and 3 are a schematic plan perspective view and a cross-sectional view of the lithium secondary battery according to exemplary embodiments, respectively.

Referring to FIGS. 2 and 3, the lithium secondary battery may include a cathode 100 and an anode 130 disposed to face the cathode 100.

The cathode 100 may include a cathode current collector 105 and a cathode active material layer 110 on the cathode current collector 105.

For example, the cathode active material layer 110 may include a cathode active material, and if necessary, a cathode binder and a conductive material.

For example, the cathode 100 may be prepared by mixing and stirring the cathode active material, the cathode binder, and the conductive material, etc. in the dispersion medium to prepare a cathode slurry, and then coating the cathode current collector 105 with the cathode slurry, followed by drying and rolling the same.

For example, the cathode current collector 105 may include stainless steel, nickel, aluminum, titanium, copper, or an alloy thereof.

For example, the cathode active material may include lithium metal oxide particles capable of reversibly intercalating and deintercalating lithium ions.

In one embodiment, the lithium metal oxide particles may contain nickel, cobalt, manganese, aluminum or the like.

In some embodiments, the lithium metal oxide particles may contain nickel, and a content of the nickel in the lithium metal oxide particles may be 80 mol % or more of all elements except for lithium and oxygen.

In some embodiments, the lithium metal oxide particles may be represented by $LiNiO_2$, $LiCoO_2$, $LiMnO_2$, $LiMn_2O_4$, or Formula 5 below.

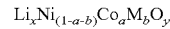

$$Li_xNi_{(1-a-b)}Co_aM_bO_y \qquad \text{[Formula 5]}$$

In Formula 5, M may be at least one of Al, Zr, Ti, Cr, B, Mg, Mn, Ba, Si, Y, W and Sr, and x, y, a and b may be in a range of 0.9≤x≤1.2, 1.9≤y≤2.1, and 0≤a+b≤0.5, respectively.

In some embodiments, in Formula 5, a and b may satisfy 0<a+b≤0.4, 0<a+b≤0.3, 0<a+b≤0.2 or 0<a+b≤0.1.

For example, the cathode binder may include an organic binder such as polyvinylidene fluoride (PVDF), vinylidene fluoride-hexafluoropropylene copolymer (PVDF-co-HFP), polyacrylonitrile, polymethyl methacrylate, etc., or an aqueous binder such as styrene-butadiene rubber (SBR). In addition, for example, the cathode binder may be used together with a thickener such as carboxymethyl cellulose (CMC).

For example, the conductive material may include a carbon-based conductive material such as graphite, carbon black, graphene, and carbon nanotubes; or a metal-based conductive material including tin, tin oxide, titanium oxide, or a perovskite material such as LaSrCoO3, and LaSrMnO3.

The anode 130 may include an anode current collector 125 and an anode active material layer 120 on the anode current collector 125.

For example, the anode active material layer 120 may include an anode active material, and if necessary, an anode binder and a conductive material.

For example, the anode 130 may be prepared by mixing and stirring the anode active material, the anode binder, the conductive material, etc. in a solvent to prepare an anode slurry, and then coating the anode current collector 125 with the anode slurry, followed by drying and rolling the same.

For example, the anode current collector 125 may include gold, stainless steel, nickel, aluminum, titanium, copper or an alloy thereof, and preferably, includes copper or a copper alloy.

For example, the anode active material may be a material capable of intercalating and deintercalating lithium ions. For example, the anode active material may include a lithium alloy, a carbon-based active material, a silicon-based active material and the like.

For example, the lithium alloy may include aluminum, zinc, bismuth, cadmium, antimony, silicon, lead, tin, gallium, indium and the like.

For example, the carbon-based active material may include crystalline carbon, amorphous carbon, carbon composite, carbon fiber and the like.

For example, the amorphous carbon may include hard carbon, cokes, mesocarbon microbead (MCMB) calcined at 1500° C. or lower, mesophase pitch-based carbon fiber (MPCF) or the like. For example, the crystalline carbon may include natural graphite, artificial graphite, graphite cokes, graphite MCMB, graphite MPCF and the like.

In one embodiment, the anode active material may include a silicon-based active material. For example, the silicon-based active material may include Si, $SiO_x$ (0<x<2), Si/C, SiO/C, Si-Metal and the like.

The anode binder and the conductive material may be substantially the same as or similar to the above-described cathode binder and the conductive material. For example, the anode binder may be an aqueous binder such as styrene-butadiene rubber (SBR). In addition, for example, the anode binder may be used together with a thickener such as carboxymethyl cellulose (CMC).

In one embodiment, a separation membrane 140 may be interposed between the cathode 100 and the anode 130.

In some embodiments, the anode 130 may have an area greater than that of the cathode 100. In this case, lithium ions generated from the cathode 100 may smoothly move to the anode 130 without precipitation in the middle.

For example, the separation membrane 140 may include a porous polymer film made of a polyolefin polymer such as ethylene homopolymer, propylene homopolymer, ethylene/butene copolymer, ethylene/hexene copolymer, ethylene/methacrylate copolymer or the like. Alternatively, for example, the separation membrane 140 may include a nonwoven fabric made of glass fiber having a high melting point, polyethylene terephthalate fiber or the like.

For example, an electrode cell may be formed including the cathode 100, the anode 130, and the separation membrane 140.

For example, a plurality of electrode cells may be laminated to form an electrode assembly 150 (however, one electrode cell is shown in FIG. 3 for the convenience illustration).

For example, the electrode assembly 150 may be formed by winding, lamination, z-folding, etc. the separation membrane 140.

The lithium secondary battery according to exemplary embodiments may include: a cathode lead 107 connected to the cathode 100 and protruding to an outside of a case 160; and an anode lead 127 connected to the anode 130 and protruding to the outside of the case 160.

For example, the cathode 100 and the cathode lead 107 may be electrically connected with each other. Similarly, the anode 130 and the anode lead 127 may be electrically connected with each other.

For example, the cathode lead 107 may be electrically connected to the cathode current collector 105. In addition, the anode lead 127 may be electrically connected to the anode current collector 125.

For example, the cathode current collector 105 may include a protrusion part (a cathode tab 106) on one side. The cathode active material layer 110 may not be formed on the cathode tab 106. The cathode tab 106 may be formed integrally with the cathode current collector 105 or may be connected thereto by welding or the like. The cathode current collector 105 and the cathode lead 107 may be electrically connected with each other through the cathode tab 106.

Similarly, the anode current collector 125 may include a protrusion part (an anode tab 126) on one side. The anode active material layer 120 may not be formed on the anode tab. The anode tab 126 may be formed integrally with the anode current collector 125 or may be connected by welding or the like. The anode current collector 125 and the anode lead 127 may be electrically connected with each other through the anode tab 126.

In one embodiment, the electrode assembly 150 may include a plurality of cathodes and a plurality of anodes. For example, the plurality of cathodes and the plurality of anodes may be disposed alternately with each other, and the separation membranes may be interposed between the cathodes and the anodes. Accordingly, the lithium secondary battery according to an embodiment of the present invention may include a plurality of cathode tabs and a plurality of anode tabs protruding from each of the plurality of cathodes and a plurality of anodes.

In one embodiment, the cathode tabs (or, the anode tabs) may be laminated, compressed, and welded to form a cathode tab laminate (or, an anode tab laminate). The cathode tab laminate may be electrically connected to the cathode lead 107. In addition, the anode tab laminate may be electrically connected to the anode lead 127.

For example, the electrode assembly 150 may be housed in the case 160 together with the electrolyte to form a lithium secondary battery.

The lithium secondary battery may be manufactured, for example, in a cylindrical shape, a square shape, a pouch type or a coin shape.

Hereinafter, preferred examples and comparative examples of the present invention will be described. However, the following examples are only preferred examples of the present invention, and the present invention is not limited thereto.

Preparative Example 1,000 g of a solvent in which ethylene carbonate (EC) and dimethyl carbonate (DMC) are mixed in a volume ratio of 3:7, and 50 g of lithium difluorophosphate ($LiPO_2F_2$) are added to a reactor and stirred, then 97 g of triethylammonium ethenesulfonate was additionally added thereto.

The reaction was carried out by stirring the mixture in the reactor at room temperature for about 7 hours. After the reaction was completed, the resulting crystals were filtered, washed with DMC, and then vacuum-dried to obtain a white target product (yield about 90%).

Three-dimensional structural analysis was performed using SC-XRD on the target product, and is shown in FIG. 1. SC-XRD analysis data are described in Table 1 below.

Through the SC-XRD analysis, it was confirmed that the target product had the desired structure (Formula 6 below).

[Formula 6]

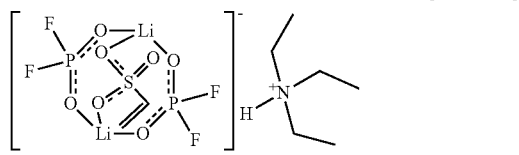

TABLE 1

| | |
|---|---|
| Empirical formula | C8H19F4Li2NO7P2S |
| Chemical formula weight | 425.12 |
| Temperature | 223(2) K |
| Wavelength | 0.71073 Å |
| Crystal system | Monoclinic |
| Space group | P2$_1$/c |
| Unit lattice dimension | a = 13.4915(13) Å b = 12.5771(13) Å |
| | c = 11.0764(11) Å |
| | α = 90° |
| | β = 96.338(3)° |
| | γ = 90° |
| Volume | 1868.0(3) Å$^3$ |
| Z | 4 |
| Density (theoretical value) | 1.512 mg/m$^3$ |
| Absorption coefficient | 0.410 mm$^{-1}$ |
| F(000) | 872 |
| Crystal size | 0.413 × 0.207 × 0.144 mm$^3$ |
| Theta range of data collection | 2.220 to 28.389° |
| Index range | −18 <= h <= 15, |
| | −16 <= k <= 16, |
| | −14 <= l <= 14 |
| Collected reflection | 25372 |
| Independent reflex | 4581 [R(int) = 0.0655] |
| Theta = level of completion up to 25.422° | 98.10% |
| Absorption correction | Semi-empirical from equivalents |
| Maximum and minimum transmission | 0.7457 and 0.5236 |
| Segmentation method | Pre-matrix least-square for F2 |
| Data/suppression/variable | 4581/0/233 |
| Goodness of fit to F2 | 1.078 |
| Final R index [I > 2sigma(I)] | R1 = 0.0587, wR2 = 0.1633 |
| R index (all data) | R1 = 0.0762, wR2 = 0.1797 |
| Intercalation coefficient | n/a |
| Maximum diffraction peak and hole | 1.097 and −0.660 e.Å$^{-3}$ |

Examples and Comparative Examples (1) Preparation of Electrolyte

A 1.0 M LiPF$_6$ solution was prepared using a mixed solvent in which ethylene carbonate (EC) and ethyl methyl carbonate (EMC) were mixed in a ratio of 3:7 (v/v).

Additives were added to the LiPF$_6$ solution in amounts according to Table 2 below based on the total weight of the electrolyte (100 wt. %), thus to prepare electrolytes of the examples and comparative examples.

(2) Preparation of Lithium Secondary Battery

A cathode slurry was prepared by mixing and dispersing Li(Ni$_{0.6}$Co$_{0.2}$Mn$_{0.2}$)O$_2$, polyvinylidene fluoride (PVdF), and carbon black in N-methyl-2-pyrrolidone (NMP) in a weight ratio of 92:4:4.

The cathode slurry was applied to an aluminum foil (thickness: 20 μm) having a protrusion part (hereinafter, a cathode tab) on one side (except for the protrusion part), then dried and rolled to prepare a cathode.

An anode slurry was prepared by mixing and dispersing crystalline artificial graphite, acetylene black and PVDF in NMP in a weight ratio of 92:1:7.

The anode slurry was applied to a copper foil (thickness: 15 μm) having a protrusion part (hereinafter, an anode tab) on one side (except for the protrusion part), then dried and rolled to prepare an anode.

A cell was formed by interposing a polyethylene separation membrane (thickness: 20 μm) between the cathode and the anode. A cathode lead and an anode lead were respectively welded and connected to the cathode tab and the anode tab, respectively.

The cell was housed in a pouch so that some regions of the cathode lead and the anode lead were exposed to an outside.

The electrolyte was injected into the pouch, followed by sealing and closing the pouch to prepare a lithium secondary battery.

TABLE 2

| | Composition and content of additive |
|---|---|
| Example 1 | Preparative example compound 0.5 wt. % |
| Example 2 | Preparative example compound 1.0 wt. % |
| Example 3 | Preparative example compound 1.0 wt. % + A-1 1 wt. % |
| Example 4 | Preparative example compound 1.0 wt. % + A-2 1 wt. % |
| Example 5 | Preparative example compound 1.0 wt. % + A-3 1 wt. % |
| Example 6 | Preparative example compound 1.0 wt. % + A-4 1 wt. % |
| Example 7 | Preparative example compound 1.0 wt. % + B-1 1 wt. % |
| Example 8 | Preparative example compound 1.0 wt. % + B-2 1 wt. % |
| Example 9 | Preparative example compound 1.0 wt. % + B-3 1 wt. % |
| Example 10 | Preparative example compound 1.0 wt. % + B-4 1 wt. % |
| Example 11 | Preparative example compound 1.0 wt. % + B-5 1 wt. % |
| Example 12 | Preparative example compound 1.0 wt. % + C-1 1 wt. % |
| Example 13 | Preparative example compound 1.0 wt. % + C-2 1 wt. % |
| Example 14 | Preparative example compound 1.0 wt. % + C-3 1 wt. % |
| Example 15 | Preparative example compound 1.0 wt. % + C-4 1 wt. % |
| Example 16 | Preparative example compound 1.0 wt. % + C-5 1 wt. % |
| Example 17 | Preparative example compound 1.0 wt. % + C-6 1 wt. % |
| Comparative Example 1 | — |
| Comparative Example 2 | A-1 1 wt. % |
| Comparative Example 3 | A-2 1 wt. % |
| Comparative Example 4 | A-3 1 wt. % |
| Comparative Example 5 | A-4 1 wt. % |
| Comparative Example 6 | B-1 1 wt. % |
| Comparative Example 7 | B-2 1 wt. % |
| Comparative Example 8 | B-3 1 wt. % |
| Comparative Example 9 | B-4 1 wt. % |
| Comparative Example 10 | B-5 1 wt. % |
| Comparative Example 11 | C-1 1 wt. % |
| Comparative Example 12 | C-2 1 wt. % |
| Comparative Example 13 | C-3 1 wt. % |
| Comparative Example 14 | C-4 1 wt. % |

TABLE 2-continued

| | Composition and content of additive |
|---|---|
| Comparative Example 15 | C-5 1 wt. % |
| Comparative Example 16 | C-6 1 wt. % |
| Comparative Example 17 | D-1 0.7 wt. % + C-1 0.3 wt. % |

A-1: vinylene carbonate
A-2: vinyl ethylene carbonate
A-3: fluoroethylene carbonate
A-4: muconic dilactone
B-1: 1,3-proane sultone
B-2: 1,3-propene-1,3-sultone
B-3: ethylene sulfate
B-4: 1,3-propanediolcyclic sulfate
B-5: 2,4,8,10-Tetraoxa-3,9-dithiaspiro[5.5]undecane 3,3,9,9-tetraoxide
C-1: lithium difluorophosphate
C-2: lithium tetrafluoro oxalate phosphate
C-3: lithium difluoro bis(oxalato) phosphate
C-4: lithium difluoro(oxalato)borate
C-5: lithium bis(oxalato)borate
C-6: lithium bis(fluorosulfonyl)imide
D-1: triethylammonium ethenesulfonate Evaluation Method 1. Evaluation of Life-Span Characteristics at 25° C.

(1) Measurement of Initial Discharge Capacity

The lithium secondary batteries of the examples and comparative examples were 1C CC/CV charged (4.2 V CUT-OFF), and 1C CC discharged (3 V CUT-OFF), then initial discharge capacity C1 was measured.

(2) Capacity Retention Rate after Repeated Charging and Discharging 500 Times

The charging and discharging processes were repeatedly performed on the lithium secondary batteries of the examples and comparative examples 500 times, then the discharge capacity C2 at the 500th time was measured.

The capacity retention rate was calculated by a percentage of C1 to C2 as follows.

The initial discharge capacity, discharge capacity at the 500th time and the capacity retention rate are described in Tables 3 and 4 below.

Capacity retention rate (%)=C2/C1×100(%)

(3) Differential Capacity Curve (dQ/dV)

The lithium secondary batteries of Example 2 and Comparative Example 1 were 0.2C CC/CV charged (4.2 V CUT-OFF), and 0.2C CC discharged (2.75 V CUT-OFF), then the charge/discharge capacity was differentiated by a voltage to deduce a relationship between the capacity curve and the voltage.

Figure 4:
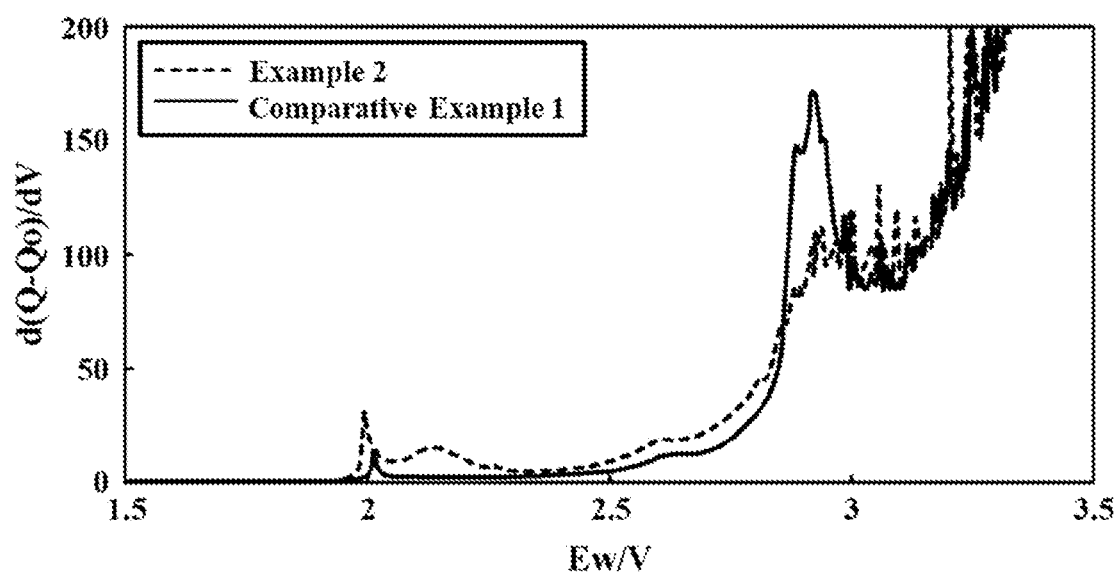
FIG. 4 is a graph illustrating differential capacity curves (dQ/dV) measured on lithium secondary batteries of Example 2 and Comparative Example 1.

The plotted differential capacity curve is illustrated in FIG. 4.

(4) AC Impedance

The lithium secondary batteries of Example 2 and Comparative Example 1 were 1C CC/CV charged (4.2 V CUT-OFF), then AC impedance was measured using an impedance analyzer.

Figure 5:
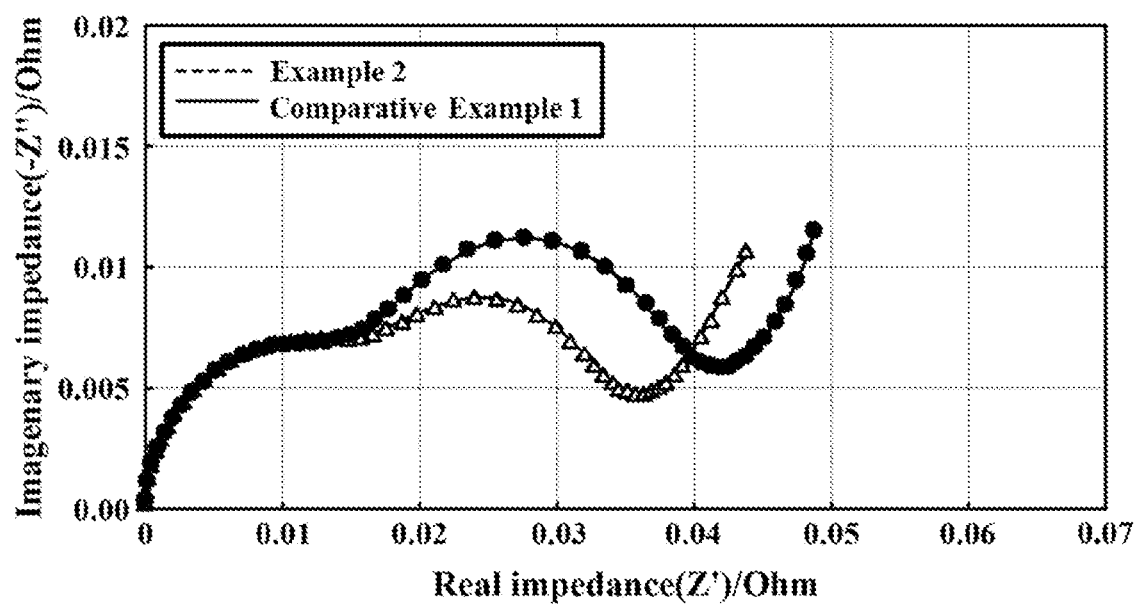
FIG. 5 is a graph illustrating alternating current (AC) impedance measured on the lithium secondary batteries of Example 2 and Comparative Example 1.

The AC impedance graph is illustrated in FIG. 5.

2. Evaluation of Output Characteristics at 25° C.

The lithium secondary batteries of the examples and comparative examples were 1C CC/CV charged (4.2 V CUT-OFF), and then 2C CC discharged to 440 mA. Thereafter, the lithium secondary batteries were discharged and supplementary charged for 10 seconds, respectively, while changing C-rate to 0.5C, 1C, 2C and 4C, then DCIR was measured.

Then, an output (pulse power) value was calculated using the measured DCIR value, and described in Tables 3 and 5 below.

TABLE 3

| | Life-span characteristic at 25° C. | | | Output characteristic at 25° C. Output (W) |
|---|---|---|---|---|
| | Initial capacity (mAh) | Capacity at 500th time (mAh) | Capacity retention rate (%) | |
| Example 1 | 879.4 | 830.2 | 94.4 | 62.1 |
| Example 2 | 878.2 | 831.7 | 94.7 | 61.5 |
| Comparative Example 1 | 873.9 | 769.0 | 88.0 | 54.2 |
| Comparative Example 17 | 876.1 | 792.9 | 90.5 | 57.2 |

As can be seen in Table 3 above, the lithium secondary batteries of Examples 1 and 2 exhibited the improved life-span characteristics and output characteristics compared to the lithium secondary batteries of Comparative Examples 1 and 17.

For example, the lithium secondary batteries of Examples 1 and 2 exhibited the improved capacity retention rate values of 3.9% to 6.4% compared to those of the lithium secondary batteries of Comparative Examples 1 and 17. In addition, the lithium secondary batteries of Examples 1 and 2 exhibited the improved output values of 7.5% to 13.4% compared to those of the lithium secondary batteries of Comparative Examples 1 and 17.

Referring to Comparative Example 17, triethylammonium ethenesulfonate reacts preferentially with lithium salt ($LiPF_6$) having high reactivity such that the compound of the preparative example was not produced. Thereby, the lithium secondary battery of Comparative Example 17 exhibited the deteriorated capacity retention rate and output value compared to the lithium secondary batteries of Examples 1 and 2.

Referring to FIG. 4, it can be seen that the compound of the preparative example is reduced and decomposed at a voltage of 2.1 V to form a solid electrolyte interface (SEI) film on the anode to suppress the decomposition of ethylene carbonate (EC) generated at a voltage of 2.9 V, such that the performance of the lithium secondary battery is improved.

Referring to FIG. 5, it can be seen that the compound of the preparative example reduce the cathode side resistance in the low-frequency region to improve the performance of the lithium secondary battery.

TABLE 4

| | Life-span characteristic at 25° C. | | |
|---|---|---|---|
| | Initial capacity (mAh) | Capacity at 500th time (mAh) | Capacity retention rate (%) |
| Example 3 | 884.8 | 856.5 | 96.8 |
| Example 4 | 882.2 | 840.7 | 95.3 |
| Example 5 | 883.4 | 843.6 | 95.5 |
| Example 6 | 880.4 | 845.2 | 96 |
| Example 7 | 879.4 | 835.4 | 95 |
| Example 8 | 879.8 | 827.9 | 94.1 |
| Example 9 | 884.3 | 853.3 | 96.5 |

TABLE 4-continued

| | Life-span characteristic at 25° C. | | |
|---|---|---|---|
| | Initial capacity (mAh) | Capacity at 500th time (mAh) | Capacity retention rate (%) |
| Example 10 | 881.4 | 833.8 | 94.6 |
| Example 11 | 881.5 | 848 | 96.2 |
| Comparative Example 2 | 879.4 | 800.3 | 91 |
| Comparative Example 3 | 878.5 | 790.7 | 90 |
| Comparative Example 4 | 878.7 | 792.6 | 90.2 |
| Comparative Example 5 | 877.7 | 792.6 | 90.3 |
| Comparative Example 6 | 876.4 | 790.5 | 90.2 |
| Comparative Example 7 | 875.9 | 787.4 | 89.9 |
| Comparative Example 8 | 879 | 799 | 90.9 |
| Comparative Example 9 | 877.5 | 793.3 | 90.4 |
| Comparative Example 10 | 877.2 | 796.5 | 90.8 |

Referring to Table 4, when using the compound of Preparative Example 1 and a specific additive in combination, it can be seen that the life-span characteristics of the lithium secondary battery are further improved.

For example, the lithium secondary batteries of Examples 3 to 11 exhibited the improved capacity retention rate values of 4.2% to 5.8% compared to the lithium secondary batteries of Comparative Examples 2 to 10.

TABLE 5

| | Output characteristic at 25° C. Output (W) |
|---|---|
| Example 12 | 64.3 |
| Example 13 | 58.5 |
| Example 14 | 62 |
| Example 15 | 62.4 |
| Example 16 | 55.2 |
| Example 17 | 60 |
| Comparative Example 11 | 60.3 |
| Comparative Example 12 | 55.9 |
| Comparative Example 13 | 58.2 |
| Comparative Example 14 | 58.3 |
| Comparative Example 15 | 51.8 |
| Comparative Example 16 | 56.8 |

Referring to Table 5, when using the compound of Preparative Example 1 and a specific additive in combination, it can be seen that the output characteristics of the lithium secondary battery are further improved.

For example, the lithium secondary batteries of Examples 12 to 17 exhibited the improved output values of 4.7% to 7.0% compared to the lithium secondary batteries of Comparative Examples 11 to 16.

For example, the compound of Preparative Example 1 may modify the structure of the SEI film on the anode formed by additives C-1 to C-6. Thereby, the life-span characteristics and output characteristics of the lithium secondary battery may be further improved.

What is claimed is:

1. A compound represented by formula 1 below:

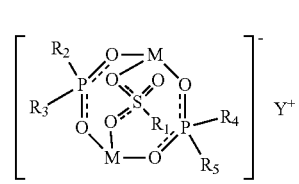

[Formula 1]

wherein, in Formula 1, $R_1$ is a C1-C6 alkyl group, a C2-C6 alkenyl group, a C2-C6 alkynyl group, a C3-C7 cycloalkyl group, or a C3-C7 cycloalkenyl group;

$R_2$ to $R_5$ are each independently halogen, or a C1-C6 alkyl group;

M is alkali metal; and $Y^+$ is a cationic material.

2. The compound according to claim 1, wherein $R_1$ is a C1-C6 alkyl group, or a C2-C6 alkenyl group;

at least one of $R_2$ to $R_5$ is halogen;

M is Li, Na or K; and $Y^+$ is $N^+RaRbRcRd$, where Ra to Rd are each independently a hydrogen or a C1-C6 alkyl group, and at least one of Ra to Rd is hydrogen.

3. The compound according to claim 1, wherein $R_1$ is a C2-C6 alkenyl group;

all of $R_2$ to $R_5$ are halogen;

M is Li; and $Y^+$ is $N^+RaRbRcRd$, where Ra is hydrogen, and Rb to Rd are each independently a C1-C3 alkyl group.

4. A method for preparing the compound according to claim 1, comprising reacting a compound represented by Formula 2 below with a compound represented by Formula 3 below:

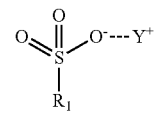

[Formula 2]

wherein, in Formula 2, $R_1$ is a C1-C6 alkyl group, a C2-C6 alkenyl group, a C2-C6 alkynyl group, a C3-C7 cycloalkyl group, or a C3-C7 cycloalkenyl group, and $Y^+$ is a cationic material; and

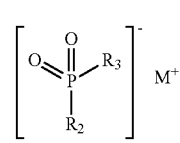

[Formula 3]

wherein, in Formula 3, $R_2$ and R3 are each independently halogen, or a C1-C6 alkyl group; and $M^+$ is an alkali metal ion.

5. An electrolyte for a lithium secondary battery, comprising:

a lithium salt;

an organic solvent; and a compound represented by Formula 1 below:

[Formula 1]

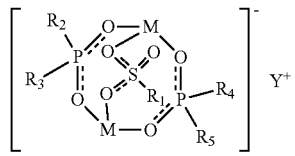

wherein, in Formula 1, $R_1$ is a C1-C6 alkyl group, a C2-C6 alkenyl group, a C2-C6 alkynyl group, a C3-C7 cycloalkyl group, or a C3-C7 cycloalkenyl group;

$R_2$ to $R_5$ are each independently halogen, or a C1-C6 alkyl group;

M is alkali metal; and $Y^+$ is a cationic material.

6. The electrolyte according to claim 5, wherein $R_1$ is a C1-C6 alkyl group, or a C2-C6 alkenyl group;

at least one of $R_2$ to $R_5$ is halogen;

M is Li, Na or K; and $Y^+$ is $N^+RaRbRcRd$, where Ra to Rd are each independently a hydrogen or a C1-C6 alkyl group, and at least one of Ra to Rd is hydrogen.

7. The electrolyte according to claim 5, wherein $R_1$ is a C2-C6 alkenyl group;

all of $R_2$ to $R_5$ are halogen;

M is Li; and $Y^+$ is $N^+RaRbRcRd$, where Ra is hydrogen, and Rb to Rd are each independently a C1-C3 alkyl group.

8. The electrolyte according to claim 5, wherein a content of the compound represented by Formula 1 is 0.01 to 10% by weight based on a total weight of the electrolyte.

9. The electrolyte according to claim 5, wherein the organic solvent includes at least one of a linear carbonate-based solvent, a cyclic carbonate-based solvent, a linear ester-based solvent, a cyclic ester-based solvent, an ether-based solvent, a ketone-based solvent, an alcohol-based solvent, and an aprotic solvent.

10. The electrolyte according to claim 5, further comprising an auxiliary additive including at least one of a fluorine-containing cyclic carbonate-based compound, a vinyl group-containing cyclic carbonate-based compound, a vinylene carbonate-based compound, a cyclic sulfate-based compound, a sultone-based compound, a fluorine-containing lithium phosphate-based compound, a lithium borate-based compound, a lactone-based compound and a sulfonyl imide-based compound.

11. The electrolyte according to claim 10, wherein a content of the auxiliary additive is 0.01 to 10% by weight based on the total weight of the electrolyte.

12. The electrolyte according to claim 11, wherein a ratio of the content of the auxiliary additive to the content of the compound represented by Formula 1 in the electrolyte is 0.1 to 10 by weight based on the total weight of the electrolyte.

13. A lithium secondary battery comprising:

a cathode;

an anode disposed to face the cathode;

a separation membrane interposed between the cathode and the anode; and the electrolyte according to claim 5.

* * * * *